US012152231B2

(12) United States Patent
Castillo et al.

(10) Patent No.: US 12,152,231 B2
(45) Date of Patent: Nov. 26, 2024

(54) SYSTEM AND METHOD FOR THE PRODUCTION OF BIOMOLECULES SUCH AS VIRAL VACCINES

(71) Applicant: UNIVERCELLS TECHNOLOGIES S.A., Nivelles (BE)

(72) Inventors: José Castillo, Brussels (BE); Bastien Mairesse, Uccle (BE); Laetitia De Viron, Ecaussinnes (BE); Jean-Christophe Drugmand, Wavre (BE)

(73) Assignee: UNIVERCELLS TECHNOLOGIES S.A., Nivelles (BE)

(*) Notice: Subject to any disclaimer, the term of this patent is extended or adjusted under 35 U.S.C. 154(b) by 582 days.

(21) Appl. No.: 16/649,687

(22) PCT Filed: Sep. 27, 2018

(86) PCT No.: PCT/EP2018/076354
§ 371 (c)(1),
(2) Date: Mar. 23, 2020

(87) PCT Pub. No.: WO2019/072584
PCT Pub. Date: Apr. 18, 2019

(65) Prior Publication Data
US 2020/0318060 A1    Oct. 8, 2020

Related U.S. Application Data

(60) Provisional application No. 62/725,545, filed on Aug. 31, 2018, provisional application No. 62/711,070, (Continued)

(51) Int. Cl.
*C12M 1/00* (2006.01)
*C12M 1/26* (2006.01)
*C12M 1/34* (2006.01)

(52) U.S. Cl.
CPC ............ *C12M 47/02* (2013.01); *C12M 29/10* (2013.01); *C12M 29/18* (2013.01); *C12M 33/14* (2013.01);
(Continued)

(58) Field of Classification Search
CPC ...... C12M 25/14; C12M 47/02; C12M 47/10; C12M 47/12
See application file for complete search history.

(56) References Cited

U.S. PATENT DOCUMENTS

| 5,503,750 A | * | 4/1996 | Russo, Jr. | ............... C12M 47/10 210/651 |
| 2006/0172417 A1 | * | 8/2006 | Rathenow | .............. B01D 63/10 435/383 |

(Continued)

FOREIGN PATENT DOCUMENTS

| CN | 104826101 A | 8/2015 | |
| EP | 0995483 A1 * | 10/1998 | ............. B01D 61/14 |

(Continued)

*Primary Examiner* — Jonathan M Hurst
(74) *Attorney, Agent, or Firm* — Dickinson Wright PLLC; Andrew D. Dorisio (57) ABSTRACT

The current disclosure concerns a system for producing biomolecules comprising a bioreactor including a chamber (1) suitable for receiving a liquid comprising cells and viral particles; and a concentrator (2), wherein said concentrator is equipped with a retentate conduit (300, 303) suitable for collecting said retentate and facilitating recirculating of the retentate to an input of said bioreactor or to an input of an intermediate vessel (4) positioned between said concentrator and said bioreactor. In a second and third aspect the disclosure concerns a method for producing biomolecules and the use of the disclosed system for the production of biomolecules.

11 Claims, 5 Drawing Sheets

Related U.S. Application Data filed on Jul. 27, 2018, provisional application No. 62/623,812, filed on Jan. 30, 2018, provisional application No. 62/564,436, filed on Sep. 28, 2017, provisional application No. 62/563,978, filed on Sep. 27, 2017.

(52) U.S. Cl.
CPC ............ *C12M 41/30* (2013.01); *C12M 41/32* (2013.01); *C12M 43/00* (2013.01)

(56) References Cited

U.S. PATENT DOCUMENTS

| | | | | |
|---|---|---|---|---|
| 2009/0130704 A1* | 5/2009 | Gyure | ................... | C12M 39/00 |
| | | | | 435/292.1 |
| 2013/0115588 A1* | 5/2013 | Davis | ................... | C12M 33/14 |
| | | | | 435/286.1 |
| 2016/0222337 A1* | 8/2016 | Serway | ................. | C12M 29/10 |

FOREIGN PATENT DOCUMENTS

| | | | | |
|---|---|---|---|---|
| EP | 2208534 | A1 | 7/2010 | |
| JP | 2003512594 | A | 4/2003 | |
| JP | 2015526094 | A | 9/2015 | |
| WO | WO-2005076093 | A1 * | 8/2005 | ............. B01L 1/025 |
| WO | 2006005305 | A2 | 1/2006 | |
| WO | 2011130617 | A2 | 10/2011 | |
| WO | 2013144091 | A1 | 10/2013 | |
| WO | 2014051503 | A1 | 4/2014 | |
| WO | 2015118148 | A1 | 8/2015 | |
| WO | 2016128361 | A1 | 8/2016 | |
| WO | 2016130940 | A1 | 8/2016 | |

\* cited by examiner

SYSTEM AND METHOD FOR THE PRODUCTION OF BIOMOLECULES SUCH AS VIRAL VACCINES

TECHNICAL FIELD

The invention pertains to the technical field of the production of viral vaccines and describes a system and method thereto.

BACKGROUND

Due to the vast number of diseases caused by pathogenic bacteria and viruses, there remains a large demand in the field to produce biomolecules such as antibodies and viruses efficiently.

The traditional methods of purifying biomolecules, especially viruses, from cultured cells are tedious and time consuming, rendering the cost of biomolecule production too high. In order to obtain products suitable for clinical administration, fast and efficient methods of producing biomolecules such as virus or viral proteins in cultured cells are needed.

The present disclosure aims to resolve at least some of the problems mentioned above. The present disclosure provides a system adapted for the purification of biomolecules with a minimum of biomolecule loss and assurance of high biomolecule quality in a restricted amount of space. Second, it is also the aim to provide a methodology with a limited amount of operational steps that still provides a high yield of biomolecule, with a significant reduction of operation expenses (OPEX) and a high level of containment.

SUMMARY

The present disclosure provides a system for producing biomolecules according to claim 1. More in particular, the disclosure provides a system for producing biomolecules comprising a bioreactor including a chamber suitable for receiving a liquid comprising cells and viral particles; and a concentrator, wherein said concentrator is equipped with a retentate conduit suitable for collecting said retentate and which allows recirculating of the retentate to an input of said bioreactor or to an input of an intermediate vessel positioned between said concentrator and said bioreactor.

More in particular the present disclosure provides a method for producing biomolecules, wherein said biomolecules are produced in a bioreactor comprising a liquid comprising cells, said method comprises a concentration step, wherein output from said bioreactor is concentrated in a concentrator and wherein output from said concentrator is recirculated to said bioreactor or to an intermediate vessel positioned between said concentrator and said bioreactor.

In another aspect, the present disclosure provides use of a system for purifying biomolecules. More in particular, the disclosure provides the use of a system for the production of viruses and/or viral vaccines.

Definitions

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight", "weight percent", "% wt" or "wt %", here and throughout the description unless otherwise defined, refers to the relative weight of the respective component based on the overall weight of the formulation.

"Biomolecule" refers to any biological material of interest that is produced in a bioreactor. Biomolecules include, for example, viruses, virus-like particles, viral products, proteins such as antibodies, carbohydrates, lipids, nucleic acids, metabolites and peptides.

"Antibody" refers to any immunoglobulin molecule, antigen-binding immunoglobulin fragment or immunoglobulin fusion protein, monoclonal or polyclonal, derived from human or other animal cell lines, including natural or genetically modified forms such as humanized, human, chimeric, synthetic, recombinant, hybrid, mutated, grafted, and in vitro generated antibodies. Commonly known natural immunoglobulin antibodies include IgA (dimeric), IgG, IgE, IgG and IgM (pentameric).

"Virus" or "virion" refers to an ultramicroscopic (roughly 20 to 300 nm in diameter), infectious agent that replicates only within the cells of living hosts, mainly bacteria, plants, and animals: composed of an RNA or DNA core, a protein coat, and, in more complex types, a surrounding envelope.

"Bioreactor" refers to any device or system that supports a biologically active environment, for example for cultivation of cells or organisms for production of a biological product. This would include cell stacks, roller bottles, shakes, flasks, stirred tank suspension bioreactors, high cell density fixed-bed perfusion bioreactors, etc.

"Purification" refers to the substantial reduction of the concentration of one or more target impurities or contaminants relative to the concentration of a target biomolecule.

"Tangential flow filtration (TFF)" refers to a method of membrane filtration in which fluid is forced through a space bounded by one or more porous membranes, where molecules small enough to pass through the pores are eliminated in the filtrate or "permeate", and molecules large enough to be rejected by the pores remain in the "retentate". The name tangential flow particularly refers to the fact that the direction of fluid flow is roughly parallel to the membrane, as opposed to so-called dead-end filtration where flow is roughly perpendicular to the membrane.

As used herein, "viral infection" refers to the entry of a virus into a cell and the subsequent replication of the virus in the cell.

"Cell culture harvest", "culture harvest" and "harvest" are used as synonyms and refer to the unclarified cell culture obtained from culturing cells in a bioreactor. The cultured cells or the grown cells also are referred to as host cells.

"Serial, in-line" means that devices or units are connected such that the outflow of one unit or device is directly fed into a subsequent unit or device, without intermediate storage.

"Isolator" or "cabinet" are used herein as synonyms and refer to a ventilated laboratory workspace for safely working with biological materials. "Isolator" includes enclosed isolators for containment of materials contaminated with (or potentially contaminated with) pathogens, enclosed biosafety cabinets for containment of materials contaminated with (or potentially contaminated with) pathogens and for protection of the product (e.g. purified target biomolecule) from contamination and laminar flow cabinets for protection of the product (e.g. a purified target biomolecule) from contamination.

DETAILED DESCRIPTION

The present invention concerns a system as well as a method for the purification of biomolecules such as proteins or viruses.

In a first aspect, the disclosure provides a system for producing biomolecules comprising a bioreactor including a chamber suitable for receiving a liquid comprising cells and viral particles, and a concentrator, wherein said concentrator is equipped with a retentate line output which collects the concentrator output and which allows recirculating of the output to an input of said bioreactor or to an input of an intermediate vessel positioned between said concentrator and said bioreactor.

In a further aspect, the disclosure provides a system for producing biomolecules comprising a bioreactor including a chamber suitable for receiving a liquid comprising a target biomolecule, a concentrator, and an intermediate vessel comprising the cell culture harvest comprising the target biomolecule in a concentration higher than the target biomolecule in the bioreactor.

This system integrates intensification technologies, thereby drastically reducing the size of each compartment and hence creating a low footprint production and purification system. The production and purification of the biomolecule can be performed as a continuous and automated process based on this system: from cell culture to final product purification minimizing human intervention. The process intensification and integration enable the containment of all compartments into an isolator ensuring the safety of process operators and the environment. The system has a small footprint. In some embodiments, the footprint of the system is less than about 50 m$^2$, 40 m$^2$, 30 m$^2$, 20 m$^2$, 10 m$^2$, 5 m$^2$, or less. In some embodiments, the footprint of the system is from about 5 m$^2$ to 10 m$^2$, 5 m$^2$ to 20 m$^2$, 5 to 30 m$^2$, 5 to 40 m$^2$, 5 to 50 m$^2$. In an example, the footprint is less than 10 m$^2$. For example, a 7 m$^2$ system can produce at least 0.5 million doses of a viral vaccine per batch, or about 107 doses per year. As a consequence, this autonomous process has a dramatic impact on the economics of biomolecule production by significantly reducing the cost of goods as well as capital expenditures.

The system for producing biomolecules of the present disclosure allows down-scaling of the infrastructure required for biomolecule production on an industrial level, thereby also allowing to reduce the amount of consumables. The system reduces the amount of consumables used by greater than or equal to about 10%, 20%, 30%, 40%, 50%, 60%, 70%, 80%, 90%, or more. The system reduces the amount of consumables used from about 10% to 20%, 10% to 30%, 10% to 40%, 10% to 50%, 10% to 60%, 10% to 70%, 10% to 80%, 10% to 90%. The system further allows to purify a biomolecule in a safe, efficient and cost-effective manner.

The system of the disclosure allows rapid production and purification of biomolecules such as recombinant proteins, viruses or viral products using significantly smaller equipment as compared to systems of the prior art. In addition, high yield of the biomolecule is obtained using the system, thereby reducing the costs of the final product. The recovery of the target biomolecule may be greater than or equal to 65%, 70%, 75%, 80%, 85%, 90%. This eventually results in a lower investment and production cost, which is a considerable advantage.

The system comprises at least one bioreactor for cell growth and/or for cells products production. In an embodiment the bioreactor is a single-use bioreactor. In another embodiment the bioreactor is autoclavable. The system is designed to be used for the growth of adherent cells, as well as non-adherent cells. In an embodiment the bioreactor is a batch bioreactor. In another embodiment the bioreactor is a perfusion bioreactor. In a perfusion bioreactor equivalent volumes of media are simultaneously added to and removed from the bioreactor, while the cells are retained in the bioreactor. This provides a steady source of fresh nutrients and constant removal of cell (waste) products. Perfusion allows to attain much higher cell density and thus a higher volumetric productivity than conventional bioreactors.

In addition, the perfusion bioreactor allows for secreted products to be continuously harvested during the process of removing media. Preferably, the bioreactor is a fixed-bed perfusion bioreactor. A fixed-bed configuration allows for a higher cell density growth to be achieved in the system and which provides for use of a bioreactor which is smaller than conventional bioreactors. Said bioreactor easily allows for a cell density of at least 50 million cells/ml to be achieved. Accordingly, the system makes use of a bioreactor which is smaller than conventional bioreactors, without compromising the high density cell culture capabilities of the bioreactor. Therefore, incorporation of a bioreactor as described allows for a reduction in terms of the space required for the system. Owing to the intensification of cell culture using this type of bioreactor the system is thus provided with a high cell density bioreactor that is small enough to be placed in an isolator. In another embodiment the system is equipped with a bioreactor suitable to be operated both in batch mode and in perfusion mode. This can be advantageous as the bioreactor in the system can be adapted to specific steps in the production and purification process e.g. the bioreactor can be operated in batch mode during inoculation, and in perfusion mode during cell growth. In another embodiment, the system comprises at least 2, 3, 4, 5, 6, 8, 10, or more bioreactors.

In a further embodiment, the currently disclosed system comprises a bioreactor and a concentrator. The concentrator allows to increase the amount of target biomolecule present in the liquid by enabling the reduction of the total liquid volume in the system without reducing the amount of target molecule in the liquid. Accordingly, implementation of a concentrator in the system of the disclosure further reduces the amount of space occupied by the system as it allows to reduce the volume of the liquid. Preferably, the concentrator comprises a filtration device or a size exclusion chromatography device.

In the current system, the concentrator is equipped with a retentate conduit suitable for collecting the retentate comprising the largest fraction of target biomolecules, and which allows re-circulation of that retentate to an input of the bioreactor or to an input of an intermediate vessel positioned between the concentrator and the bioreactor. The current system thus allows re-circulating of the concentrated retentate for further concentration of the biomolecule by allowing re-circulation of the retentate through the same concentrator. In an embodiment, the liquid is re-circulated through the concentrator at least 5 times, preferably at least 10 times, more preferably at least 15 times, most preferably until the desired reduction in cell culture harvest is reached. This set up allows the system to reduce the amount of downstream processes needed as a highly concentrated biomolecule product is obtained due to re-circulation of the retentate. In an embodiment, the conduits of the system comprise pumps, valves and flow meters or sensors to control and monitor the flow of liquid from, for example, the concentrator to the bioreactor and/or intermediate vessel. In an embodiment, the system's conduits, such as the retentate conduit, comprise detectors (e.g., optical detectors). In an embodiment, the detectors can monitor the amount of cells, target biomolecules, and/or contaminants that are transported in the conduits.

The volume of the intermediate vessel is preferably adapted to the volume of the bioreactor. The retentate comprising the concentrated target biomolecule is eventually harvested in the intermediate vessel. When, for example, the system is equipped with a bioreactor with a capacity of around 10 L that uses 300 L of culture medium in perfusion mode, that system will preferably be equipped with an intermediate vessel with a volume of around 10 L.

In an embodiment, the bioreactor and the concentrator are connected by a conduit facilitating liquid transport from said bioreactor to said concentrator. Alternatively, when an intermediate vessel is included in the system, the bioreactor and the intermediate vessel are connected by a conduit, facilitating liquid transport from the bioreactor to said intermediate vessel. In addition, the intermediate vessel and the concentrator are also connected by a conduit which allows liquid transport from the intermediate vessel to the concentrator. Finally, a conduit facilitating liquid transport from the concentrator to the bioreactor can also be provided. In an embodiment the intermediate vessel may be single-use, disposable or autoclavable.

The system's concentrator can be a chosen from a number of devices known to the skilled person which are suited for reducing the volume of the liquid in which the target biomolecule resides. In some embodiments, the concentrator comprises one type of concentration device (e.g., tangential flow filter). In some embodiments, the concentrator comprises more than one type of concentration device (e.g., tangential flow filter and dead-end filter). Most of these devices are based on filtration and/or size exclusion chromatography. In one embodiment the concentrator is a filtration device, more preferably a micro-filtration device, or an ultra-filtration device or a combination of both micro- and ultra-filtration device. When the system is provided with an ultra-filtration device for reducing the volume of the liquid in which the target biomolecule resides, the membrane of the device is adapted as to allow flow through of water and low molecular weight solutes, which are in general referred to as the permeate, while macromolecules such as biomolecules are retained on the membrane in the retentate. In a further embodiment, the system is provided of a tangential flow filtration device (TFF). In an embodiment, said TFF is equipped with at least one hollow fiber having pores with a porosity sufficient to retain practically all of the target biomolecules, while permitting smaller contaminants such as growth medium and solutes to pass through the pores of the membrane. In contrast to dead-end filtration, in which the liquid is passed through a membrane or bed, and where the solids are trapped on the filter, tangential flow across the surface of the filter is allowed in the TFF device, rather than directly through the filter. Accordingly, formation of a filter cake in the TFF is avoided. In another embodiment, said TFF may be equipped with a cassette allowing tangential flow filtration. In yet another embodiment, said TFF is a single pass tangential flow filtration (SP-TFF). This device is especially advantageous when purifying proteins such as antibodies.

As mentioned above, the system is provided with a retentate conduit mediating re-circulating of the retentate to an input of the bioreactor or an input of an intermediate vessel. An additional advantage of implementing a TFF device as a concentrator in the system is that the TFF device is suited to be operated in a continuous perfusion process. This allows significant concentration of the culture volume. For example, when starting from a fixed bed perfusion bioreactor with a 500 $m^2$ internal growth area (referring to the surface area accessible for cell growth), the system allows concentrating the culture volume to a final volume of 50 L. This is the equivalent of a classical 1000 L microcarrier based culture or 6000 roller bottles based culture and thus a significant improvement over the prior art, not in the least as it allows reduction of the footprint of the system. The size reduction of the system allows for production of biomolecules to be performed in a highly contained and sterile environment, assuring the sterility of operations.

In an embodiment the conduits of the system are fitted with one or more pumps to provide directional liquid flow and to allow control or induce differential pressure between different parts of the system. In a further embodiment, the pumps can operate both forward and backwards. In a still further embodiment, the conduits of the system are preferably fitted with one or more pumps to provide cross-flow of the liquid through the concentrator.

The conduits of the system here disclosed, may be provided with sensors for measuring parameters important for cell growth and for the purification process including but not limited to liquid flow rate, temperature, pH, oxygen saturation and pressure. In addition conduits of the system may be provided with valves to control flow distribution. The valves further allow engaging or disengaging a specific system segment or conduit. In some embodiments, the valves are metered valves or discrete valves (e.g., on or off valves). In an example, the valves are discrete valves. In some embodiments the valves allow sampling of the liquid from the respective conduit, for example for quality control.

In an embodiment, the system is provided with a pre-filter which is positioned between the bioreactor and the concentrator. In some embodiments, the system includes at least 1, 2, 3, 4, 5, 6, 8, 10, or more pre-filters. In some embodiments, the pre-filters may have the same porosity or the pre-filters may have different porosities. In an example, the system has at least 2 pre-filters of differing porosity. The pre-filter prevents clogging of the concentrator. The pre-filter thereto preferably has a pore size of at least 50 µm, at least 75 µm, at least 100 µm, at least 125 µm and at most 250 µm, at most 200 µm, at most 175 µm, at most 150 µm. In a preferred embodiment the filter has a pore size of 125 µm. A pore size which is smaller than 50 µm will not permit sufficient liquid flow rate whereas a pore size which is above 250 µm would risk the flow through of liquid containing particles which might clog the system. In an embodiment, the pore size of the pre-filters is significantly larger than the biomolecule and is sized to retain cells debris and aggregates. In an embodiment, said pre-filter may be a TFF, wherein the particles larger than said biomolecule of interest are retained, whereas smaller particles, including the biomolecule, will pass through said TFF. In another embodiment, said pre-filter may be an adsorption system, for example an adsorption system based on chromatography.

When an intermediate vessel is included in the system, the pre-filter described above is preferably positioned between the bioreactor and the intermediate vessel. Accordingly, the system allows that the conduits between the intermediate vessel and the concentrator remain free of particles which due to their size could potentially clog the concentrator.

Undesired material that is produced in the system or by-products of the process can be temporarily stored in a decontamination vessel. The system may comprise one or more decontamination vessels and may be adapted with suitable conduits such as an output conduit line from the concentrator to the decontamination vessel(s) in order to discard the permeate. In some embodiments, the system comprises at least 1, 2, 3, 4, 5, 6, 8, 10, or more decontamination vessels. Another example is an output conduit line from the bioreactor to the decontamination vessel to directly discard liquids before the production of the biomolecule has started (e.g. before viral infection of the cells).

In addition to the production and purification of biomolecules (e.g. upstream production processes), the system can be adapted to further include devices suitable for performing downstream production processes. The system of the disclosure can thereto comprise a clarification compartment. This clarification compartment need not be physically separated from the foregoing described devices such as the bioreactor and the concentrator and will be in fluent connection with the latter. Clarification can be considered the first step of downstream processing and ensures removal of cell debris and other contaminants from the previously harvested retentate. In some embodiments, the clarification compartment includes at least 1, 2, 3, 4, 5, 6, 8, 10, or more filters. In some embodiments, the clarification compartment includes a single type of filter. In some embodiments, the clarification compartment includes multiple types of filters. In a further embodiment the clarification compartment comprises one or more filters selected from depth filters, filters comprising diatomaceous earth as filter aid, microfilters and functional filters such as filters based on anion exchange chromatography, size exclusion chromatography, hydrophobic interaction chromatography and mixed-mode chromatography. In an example, the clarification compartment comprises an anion exchange depth filter and a microfiltration device. Clarification provides for the removal of remaining cell culture impurities such as host cell DNA and protein residues. Accordingly, this setup allows residual solid contaminants to be removed from the product stream therefore assuring the correct functioning of the subsequent purification compartments. Due to the use of the concentration step as described above, wherein retentate is re-cycled from the concentrator to the bioreactor or intermediate vessel, the clarification compartment will be smaller in size (compared to the prior art) allowing compact compartment operation and reduction in processing time, thus benefiting the overall economics of the biomolecule production and purification process. In some embodiments, the clarification compartment is at least 50%, 75%, 80%, 85%, smaller than a clarification compartment in a system without a concentrator. Accordingly, use of the system comprising a concentrator, allows to reduce the size of the clarification compartment to at most 80%, 60%, 50%, 40%, 30%, 20% of the required size in the absence of a concentrator in the system.

The currently disclosed system can, in another or further embodiment comprise a chromatography compartment, wherein the chromatography compartment and the clarification compartment are connected by a conduit facilitating liquid transport from the clarification compartment to the chromatography compartment. The chromatography compartment allows further purification of the target biomolecule and comprises at least one chromatography device. In an embodiment, the chromatography compartment comprises a single chromatography device which offers a high binding capacity, capable of processing a large input volume in a limited number of cycles. In some embodiments, the chromatography equipment is at least 50%, 75%, 80%, 85%, smaller than the chromatography equipment in a system without a concentrator. Accordingly, use of the system comprising a concentrator, allows to reduce the size of the chromatography device to at most 80%, 60%, 50%, 40%, 30%, 20% of the required size in the absence of a concentrator in the system. In an embodiment the chromatography compartment comprises absorber systems and/or one or more tangential flow filtration devices in series. In another embodiment, the chromatography compartment comprises a mixed mode chromatography membrane which is suited for continuous mode operation. Due to the volume reduction ensured by the first part of the system as disclosed, the required chromatography membrane volume in the chromatography compartment is smaller than in the systems of the prior art. Accordingly, the system allows to cut down on costs relating to expensive large chromatography equipment. Additionally, in contrast to biomolecule production and purification systems of the prior art, which usually require the presence of two consecutive chromatography devices, the system of the present disclosure assures equivalent biomolecule purity and yield by implementing a single-step chromatography device in the chromatography compartment. This results in a remarkable reduction in biomolecule production footprint, production costs and production time thus enhancing the productivity, while a low process volume can be maintained throughout the system. For example, a conventional polio vaccine production system of the art with a footprint of 5000 m² may have a capacity of 60 million doses/year with a production cost of 1.2-1.5 USD/dose and a processing time of at least 5 weeks. A system for producing a polio vaccine according to an embodiment of the current disclosure may have a footprint of 1500 m² and a production capacity of 40 million doses/year at a production cost of 0.22 USD/dose and a production time of around 3 weeks.

In an embodiment the biomolecule produced and purified in the system of the disclosure is a purified inactivated virus. Accordingly, the system can thereto implement a viral inactivation compartment, wherein the viral inactivation compartment and the chromatography compartment are connected by a conduit facilitating liquid transport from the chromatography compartment to the viral inactivation compartment. Viral inactivation is, in an embodiment wherein the target biomolecule is a viral particle, obtained by diluting the purified virus that is obtained after chromatography with formaldehyde.

In an embodiment the process flow from the bioreactor to the concentrator is controlled by a process controller or process control device. The controller controls and operates bioreactor parameters as well as process flow parameters and monitors and records data from one or more sensors described above (pH, temperature and/or DO). Said controller furthermore controls the functioning of the concentrator and the recirculation of retentate from concentrator to intermediate vessel and back. To that purpose, said controller is provided with software allowing monitoring, controlling and recording the process flow and parameters of the system. The controller is able to manage liquid flow through the subsequent parts of the system thereby controlling the production and purification of the target biomolecule. Preferably, liquid flow is managed by the controller in the system by controlling the functioning of the pumps and or valves present therein. In an embodiment the process control device provides automated control of the system's process flow.

Access to the controller can be provided to the user via a computer which can be connected to the controller. The controller allows export of data through one or more data transfer devices which can be wireless such as a Wifi or Bluetooth connection or wired such us a USB connection present on said controller. Data connections on the controller can in another or further embodiment allow access to an IT network. In a further embodiment, a screen is connected to the controller which allows the system's user or operator to follow the process flow and measured parameters as well as to manually operate the system, e.g. by starting or stopping certain sub-processes.

In a further or other embodiment, the controller can be integrated in a docking station which encompasses the above described bioreactor (1), concentrator (2) and intermediate vessel (4). Integration of the controller in a docking station allows to maintain the compactness of the system when it is included in the system.

Due to the optimization of each compartment in the system of the present disclosure, the compact structure of each compartment allows all compartments belonging to the system to be incorporated in a single cabinet, isolator or containment enclosure. This not only contributes to reduction of space required but also to the enhanced safety when using this system. In addition, the connections between the compartments allow the production and purification steps to be performed without exiting the containment enclosure thus ensuring minimal safety risks.

The compact structure of the system further allows, in another or further embodiment, to provide the system as a portable system for biomolecule production and purification system e.g. in a container or trailer. Therefore, the current system can be a mobile system. In another or further embodiment, the compartments of the platform can also be mobilized, for example, by placing each compartment or isolator on a mobile skid. In yet another embodiment, the system can be assembled in a modular fashion.

In another or further embodiment the system further comprises a containment enclosure, wherein one or more of the compartments, isolators and/or systems as disclosed herein are housed in the containment enclosure. In some embodiments, this containment enclosure is provided with at least one entrance through which users and/or materials enter the containment enclosure and at least one exit through which users and/or materials exit the containment enclosure. The entry means and exit means of the containment enclosure are opened or closed automatically by a process control device or process controller which collects, monitors and/or records data on actions performed by the compartments of said system. The process controller thereto locks or unlocks the entrance or exit upon input signals generated by the process, such as the termination of a certain task (e.g. virus inactivation). Automatic control of exit from and entry into the containment enclosure guarantees opening of the containment enclosure only under safe conditions. In an embodiment, the system comprises multiple control devices. In another or further embodiment, the systems' compartments are placed in isolators within the containment enclosure. The isolated compartments can be connected to or separated from one another by partitions present between these isolators and which partitions, when present, can be in an open configuration or a closed configuration. In an open configuration, access from one isolator to the other is allowed. Access to and/or between the isolators is thus regulated via the opening and closing of said partitions. In another embodiment the compartments are placed in a single isolator and are separated from each other by partitions which can be brought in an open and closed configuration, thereby either allowing or blocking access and transport of material or fluids from one isolator to the other. Opening and closing of said partitions may also be automatically controlled by the process control device or process controller upon input signals generated by the process, such as the termination of a certain task (e.g. virus inactivation), in order to further assure the safe use of the system. Said partitions can be provided with openings for allowing passage of conduits such as tubings or pipings.

The partitions and/or entrance and/or exit means can be made from a strong material, for example, aluminum, stainless steel, fiber glass or any other suitable material. The partitions and/or the entrance and/or exit means can include lift gate type doors, swing doors, shutters or sliding doors, and can include glass or Plexiglas panels. The isolators and containment system are manufactured and assembled according to European and US standards and isolate the internal environment from the external environment.

A suitable access mechanism, for example, a lock and key mechanism, a pass code punch pad, card swipe, transponder reader, finger print scanner, retina scanner, sensors, automatic identification and data capture methods such as radio-frequency identification (RFID), biometrics (like iris and facial recognition system), magnetic stripes, Optical character recognition (OCR), smart cards and voice recognition, or any other access mechanism, can be provided to unlock the partitions and/or the entrance and/or the exit.

Preferably, users that enter the system remain outside the isolated compartments. In order to allow sample taking for quality control procedures, the isolated compartments are, in an embodiment, provided with flexible sleeves through which the user is allowed limited indirect access to the compartments, whose content remain isolated from the user. These further containment and isolation measures allow the system to be used for production and purification of biomolecules that constitute a high risk for the user. For example, the system is suited for the purification of large quantities of live virus needed for the manufacture of vaccines consisting of inactivated purified virus. For the latter, high level BSL-3 containment is required.

Integration of isolators and containment enclosures as part of the system, renders compliance with biological safety rules simpler and less costly, reducing the risks of contamination for the environment and the operators.

In an embodiment, said system for producing biomolecules comprises:

An upstream process compartment comprising a fixed-bed perfusion bioreactor including a chamber suitable for receiving a liquid comprising cells; and a concentrator, preferably a TFF wherein said concentrator is equipped with a retentate conduit suitable for collecting a liquid output such as a retentate from said concentrator and recirculating said liquid output to an input of said bioreactor or to an input of an intermediate vessel positioned between said concentrator and said bioreactor;

a clarification compartment;

a chromatography compartment; and optionally a viral inactivation compartment;

wherein said compartments are located in one or more isolators. In some embodiments, the compartments are located in at least 1, 2, 3, 4, 5, 6, 8, 10, or more isolators. In some embodiments, the isolator may contain a single compartment or more than one compartments.

In an example, the system comprises at least a first isolator comprising an upstream process; and a second isolator comprising a downstream process, wherein the second isolator comprises a clarification compartment and a chromatography compartment.

By preference, said system comprises at least three isolators: A first isolator will comprise said upstream process; a second isolator comprising said clarification compartment and chromatography compartment and a third isolator comprising said inactivation compartment. Said first isolator will preferably be in fluent communication to said second isolator, and said second isolator will preferably be in fluent communication with said third isolator.

Said isolators may furthermore be connected to or separated from one another by partitions wherein said partitions can be brought in an open or closed configuration. This has been extensively discussed above.

In a final embodiment, the isolators will be comprised in a containment enclosure as described above.

In an embodiment, the disclosure provides a system for producing viruses comprising: a fixed-bed perfusion bioreactor including a chamber suitable for receiving a liquid comprising cells and viral particles; and a hollow fiber tangential flow filtration (TFF) device, wherein said TFF is equipped with a retentate conduit suitable for collecting said retentate and facilitating re-circulating of the retentate to an input of said bioreactor or to an input of an intermediate vessel positioned between said TFF and said bioreactor.

In a second aspect the disclosure provides a method for producing biomolecules, wherein said biomolecules are produced in a bioreactor comprising a liquid comprising cells, said method comprises a concentration step, wherein output from said bioreactor is concentrated in a concentrator and wherein output from said concentrator is recirculated to said bioreactor or to an intermediate vessel positioned between said concentrator and said bioreactor. It will be apparent to a skilled person that the system as described in one of its embodiments is suited for executing said method.

In an embodiment, the method for producing biomolecules according to the present disclosure makes use of pumps and valves, which are fitted on the conduits of the system, to induce directional flow of the liquid through the system and to allow reversible engaging and disengaging of different segments of the system. In some embodiments, the disclosed method makes use of an ultrafiltration device in the concentrator. To avoid clogging of the ultrafiltration device present in the concentrator, the liquid is first passed through a pre-filter which removes large solid particles from the liquid but is permeable to the biomolecule of interest. In some embodiments, the pre-filter has a pore size of approximately 125 µm and a cutoff of approximately 100 kDa. Preferably, the recirculated retentate is harvested in an embodiment of the method by collecting it in the intermediate vessel, thereby obtaining a concentrated cell culture harvest. In an embodiment, parts of the system such as the bioreactor and the intermediate vessel may be provided with one or more sensors for measuring for instance but not limiting to the pH, temperature and the dissolved oxygen. Accordingly, the bioreactor and intermediate vessel may allow control of pH, and temperature of the concentrated cell culture harvest.

Optionally, the pH of the concentrated cell culture harvest is adjusted to the desired value for downstream processes. In addition an optional endonuclease treatment can be performed on the concentrated cell culture harvest to degrade DNA and RNA present in the concentrated cell culture harvest while leaving proteins intact. An endonuclease treatment step can contribute to the prevention of aggregation in the concentrated cell culture harvest, thus providing optimal conditions for further downstream processing.

In an embodiment, said method further comprises downstream processing steps which can include clarification of the concentrated cell culture harvest thereby obtaining a clarified cell culture harvest and/or subsequent purification of the desired biomolecule by performing a chromatography step on the clarified cell culture harvest.

As mentioned above, the currently disclosed method can be performed in a restricted amount of space due to the compactness of the required equipment, and thus can be performed within isolators and even within a containment enclosure. Therefore, the method of the present disclosure is especially well suited to purify biomolecules, such as proteins (antibodies) and viruses. In that last case, the method further includes a virus inactivation step performed on the purified viral product, preferably consisting of treatment of the virus with an inactivation composition. The inactivation compositions are selected from the group comprising formaldehyde, at least one detergent, at least one acid or any combination thereof. Other inactivation compositions may comprise a potassium persulfate solution (commercially known as Virkon®), sodium hydroxide or bleach. Preferably, formaldehyde or formalin is used for viral inactivation. Accordingly, and in a further preferred embodiment of the disclosed method, the purified biomolecule is a purified inactivated virus, used for the formulation of a vaccine, such as for example an inactivated polio virus vaccine. The method of the disclosure is especially well suited for the production and purification of biomolecules wherein the biomolecules are viruses or inactivated viral particles.

The currently described method and system ensures a very high safety level and very low degree of health or environmental risks associated with the use of said method and system. Accordingly, and in a further aspect, the disclosure relates to the use of a system as described above for the production of viruses and/or viral vaccines.

It is supposed that the present invention is not restricted to any form of design described previously and that some modifications can be added to the presented examples without reappraisal of the appended claims. For example, the present invention has been described referring to Polio vaccine, but it is clear that the invention can be applied to Rotavirus vaccine, for instance or to Rabies vaccine.

Detailed Figure Description

Figure 1:
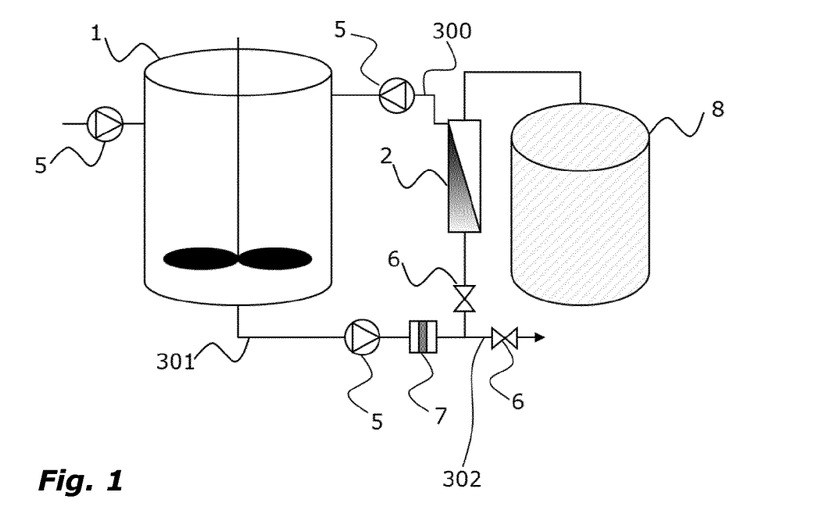
FIG. 1 shows a schematic overview of a system for producing biomolecules according to an embodiment of the disclosure.

FIG. 1 shows a schematic overview of a system for producing biomolecules according to an embodiment of the disclosure.

The schematic overview is shown of a system for producing biomolecules comprising a bioreactor (1) comprising a cell culture, wherein the cell culture may comprise a liquid comprising cells and viral particles; and a concentrator (2), wherein said concentrator is equipped with a retentate line output (300) which collects the concentrator output and which allows re-circulating of the output to an input of said bioreactor (1). The bioreactor (1) and the concentrator (2) are connected by a conduit (301) facilitating liquid transport from said bioreactor (1) to said concentrator (2). To avoid clogging of the concentrator (2), the liquid is first passed through a pre-filter (7) which removes large solid particles from the liquid but is permeable to the biomolecule of interest. The conduits of the system are fitted with pumps (5) to provide directional liquid flow, for controlling or inducing differential pressure between different parts of the system and to provide cross-flow of the liquid through the concentrator (2). In addition, the conduits of the system are provided with valves (6) to control flow distribution. The valves further allow to engage or disengage a specific system segment or conduit. Finally, an output conduit (302) line from the concentrator (2) to a decontamination vessel (8) is provided to discard the permeate. The decontamination vessel (8) comprises at least one waste container (such as a tank) where undesired material that is produced in the system or by-products of the process can be temporarily stored.

The concentrator provides for an increase of the amount of target biomolecule present in the liquid by enabling the reduction of the total liquid volume without reducing the amount of target molecule in the liquid. The current embodiment of the disclosed system thus provides for re-circulating of the concentrated liquid retentate comprising the target biomolecule, for further concentration of the biomolecule by allowing re-circulation of the liquid through the same concentrator (2). This set-up allows for the design of the overall system to fewer numbers of downstream processes needed as a highly concentrated biomolecule product is obtained due to re-circulation of the liquid.

Figure 2A:
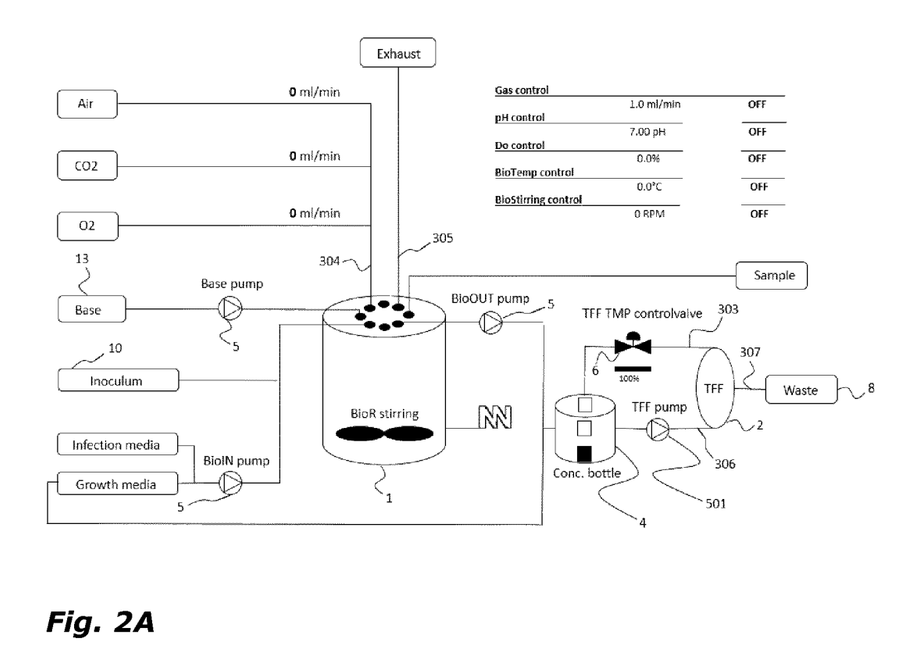
FIG. 2A shows a schematic overview of a system for producing biomolecules according to another embodiment of the disclosure.

FIG. 2A shows a schematic overview of a system for producing biomolecules according to another embodiment of the disclosure.

The schematic overview is shown of a system for producing biomolecules comprising a bioreactor (1) including a chamber suitable for receiving a liquid comprising cells and viral particles, and a concentrator (2), wherein said concentrator is equipped with a retentate line output (303) which collects the concentrator output and which allows re-circulating of the retentate output to an input of an intermediate vessel (4) or concentrator bottle positioned between said concentrator (2) and said bioreactor (1). The bioreactor (1) and the intermediate vessel (4) are connected by a conduit, facilitating liquid transport from the bioreactor (1) to said intermediate vessel (4). Alternatively, an additional conduit connected directly from the bioreactor (1) to the concentrator (2) could be present (not shown on figures) for transporting liquid from the bioreactor (1) to the concentrator (2). In addition, the intermediate vessel (4) and the concentrator (2) are also connected by a conduit (306) having pump (5) which facilitates liquid transport from the intermediate vessel (4) to the concentrator (2). The concentrator enhances the amount of target biomolecule present in the liquid by enabling the reduction of the total liquid volume without reducing the amount of target molecule in the liquid.

In an embodiment two gas connections are present, one connection (304) entering the bioreactor (1) and one connection (305) exiting said bioreactor (1). The bioreactor (1) is further connected with the inoculum vessel (10) comprising the rinsed, detached and neutralized cell preculture in suitable growth medium, and a base (13) inlet for regulation of the pH inside the bioreactor (1).

Multiple types of concentrators are suitable for use in the system, the system according to this embodiment, is provided with a tangential flow filtration device (TFF) acting as the concentrator. The TFF is equipped so that it retains practically all of the target biomolecules, while permitting smaller contaminants such as growth medium and solutes to pass through the pores of the membrane. To that purpose and in a possible embodiment, said TFF may be provided with at least one hollow fiber having pores with a specific porosity, e.g. a porosity sufficient to retain practically all of the target biomolecules in the retentate, while permitting smaller contaminants such as growth medium and solutes to end up in the permeate. The TFF concentrator (2) mediates re-circulating of the retentate comprising the target biomolecule to an input of the intermediate vessel (4). An output conduit (307) line from the TFF concentrator (2) to a decontamination vessel (8) is provided to discard the permeate. The decontamination vessel (8) comprises at least one waste container such as a tank where undesired material that is produced in the system or by-products of the process can be temporarily stored. The system conduits are fitted with pumps (5, 501) and valves (6) to provide directional liquid flow, to control differential pressure between different fragments of the system and to provide cross-flow of the liquid through the TFF concentrator (2).

The concentrator (2) increases the amount of target biomolecule present in the liquid by enabling the reduction of the total liquid volume without reducing the amount of target molecule in the liquid. Reduction of the liquid volume by the system allows down-scaling of the infrastructure required for biomolecule production on an industrial level, thereby also reducing the amount of consumables. In addition, the TFF concentrator (2) of this system is operated autonomously in a continuous perfusion mode. This results in a minimization of human intervention, thereby limiting the safety risks and reducing expenditures.

Figure 2B:
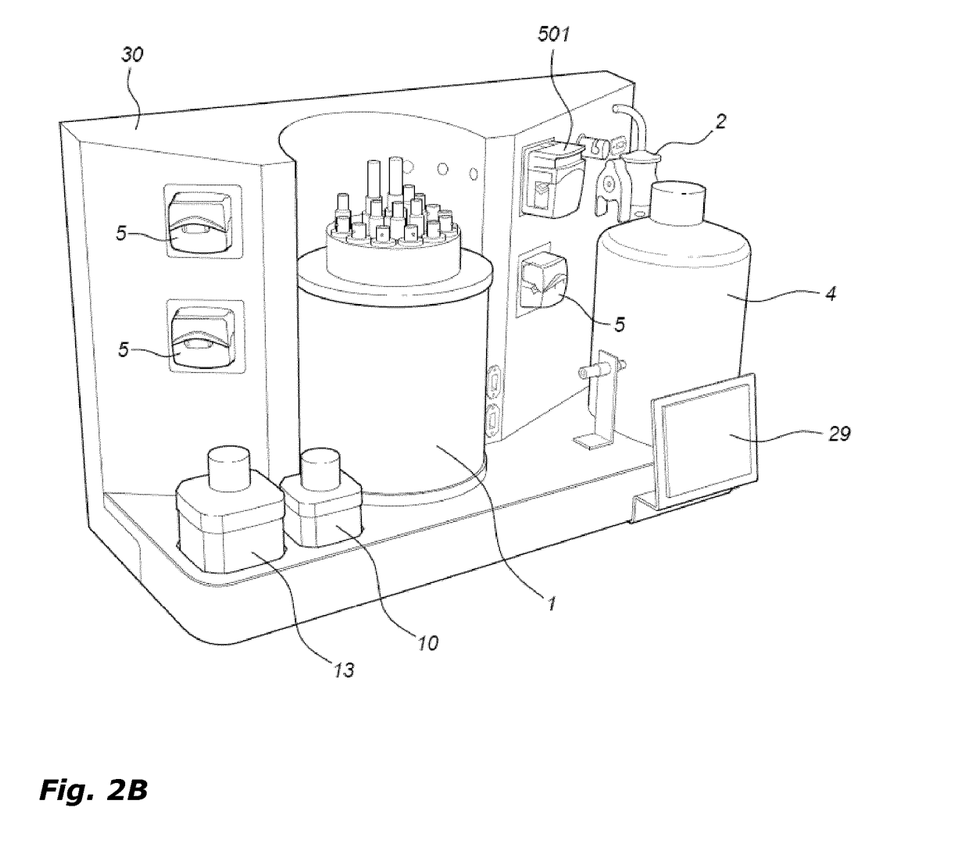
FIG. 2B shows an embodiment of a system able to execute the scheme given in FIG. 2A.

FIG. 2B shows a system able to execute the scheme shown in FIG. 2A.

The system is designed to be used in a biosafety cabinet or isolator and can be used for both process development work and pilot-scale production of biological material, in which case it can be used to produce material for clinical trials as well as low volume commercial production. The system is designed to be used for the growth of adherent cells, as well as non-adherent cells. To that purpose, the system comprises a bioreactor (1), preferably a fixed bed bioreactor. The fixed bed of the bioreactor can be provided with structural elements for allowing growth of the cells on the surface of said elements. An example of such elements is given in PCT/EP2017/078775 which is incorporated herein by reference and which describes a spiral structure for allowing growth of cells and promoting fluid distribution and turbulence. The elements can be made of polyethylene, preferably hydrophilized polyethylene. In an embodiment the bioreactor (1) is for single-use only. Conduits present in the system for liquid or gas transport are not shown in the figure. The bioreactor (1) has at least two fluid connections, wherein one connection allows entrance of fluid into the bioreactor and a second connection allows removal of fluid. This last connection is designed in such way that it minimizes dead space inside the bioreactor (1) once emptied. In a further embodiment, said bioreactor (1) is provided with gas connections, for allowing entrance and/or exit of gas. In a preferred embodiment, three gas connections are present, two connection entering the bioreactor (1) and one connection exiting said bioreactor (1). Advantageously, the bioreactor (1) is furthermore designed to allow sampling for both in-process control and for end of process analysis, preferably from the top of said bioreactor (1). Sampling can occur via syringes or equivalent assemblies.

Circulation in the bioreactor (1) is achieved by use of an impeller, preferably a magnetically driven impeller. A heating element may be present to heat the content of said bioreactor (1), or to heat medium that is brought into said bioreactor (1). The lid of the bioreactor (1) is provided with one or more sensors for measuring temperature, pH and/or dissolved oxygen in said bioreactor (1).

Liquid output from the bioreactor (1) will be transferred by means of a conduit to an intermediate vessel (4) also known as concentrator bottle. Such intermediate vessel (4) may be a PET bottle, and may hold a volume of about 500 mL to 5000 mL. This intermediate vessel (4) is connected to a concentrator (2) which may be a TFF. Liquid from the intermediate vessel (4) comprising the target biomolecule will be transported to the concentrator (2) by means of a pump (501). Said pump (501) is, in an embodiment, able to provide a shear rate of 2000 $s^{-1}$ inside the concentrator (2). The retentate of the concentrator (2) will subsequently be brought back to the intermediate vessel (4), whereas liquid waste will be discarded (preferably to a waste bottle, not shown on FIG. 2B). Due to the re-circulation of retentate back and forth from the intermediate vessel (4) to the concentrator (2), a heavily concentrated biomolecule product will be obtained, which can be used for further downstream processing (such as chromatographic purification) or as source for trials such as e.g. clinical trials.

The process flow from bioreactor (1) to concentrator (2) is controlled by a process controller. In order to maintain the compactness of the system, especially considering it is sized to be used inside a biosafety cabinet or isolator, the controller is integrated in a docking station (30) which is designed to receive the above-described bioreactor (1), concentrator (2) and intermediate vessel (4). The controller controls and operates bioreactor parameters as well as process flow parameters and monitors and records data from one or more sensors described above (pH, temperature and/or DO). Said controller further controls the functioning of the concentrator (2) and the recirculation of retentate from concentrator (2) to intermediate vessel (4) and back, preferably by controlling the functioning of the pump(s) (5, 501) between intermediate vessel (4) and concentrator (2).

To that purpose, said controller is provided with software allowing monitoring, controlling and recording the process flow and parameters of the system. Access to the controller can be provided to the user via a computer which is pluggable to the controller. The controller allows export of data through one or more USB connections present on said docking station and allows access to an IT network. A screen (29) such as a touch screen present on the docking station allows the user to follow the process flow and measured parameters as well as to manually operate the system, e.g. by starting or stopping certain sub-processes.

As described above, the docking station (30) with integrated controller further allows for docking of a bottle for supply of base (13) to the bioreactor (1). Such bottle may be a PET bottle, with a volume of between 500 mL to 5000 ml. Said docking station (30) may further allow docking of a bottle for supply of inoculum (10)/additive (not shown) to the bioreactor (1). A retention tray for catching potential liquid overflows can be provided.

The docking station (30) will be preferably constructed out of a material that allows cleaning with a NaOH (such as 0.5 M NaOH) solution, alcohols such as ethanol or virucides such as Virkon. The docking station (30) should equally be able to resist a sterilizing regime using vaporized hydrogen peroxide (VHP). In a preferred embodiment, the material of said docking station (30) is a corrosion resistant metal. The docking station (30) can be powered by a power supply, such as a standard 110-230V, 50-60 Hz power supply.

Hence, the current disclosure is also directed to a portable biomolecule production facility, comprising a bioreactor and a concentrator such as a TFF, wherein an intermediate vessel is positioned between said bioreactor and concentrator, and wherein said intermediate vessel and concentrator are connected by a retentate conduit, allowing recirculating of liquid from an output of the concentrator to an input of said intermediate vessel and wherein said bioreactor, concentrator and intermediate vessel are present in a portable docking station, said docking station comprises an integrated controller, able to control the biomolecule production process.

Figure 3:
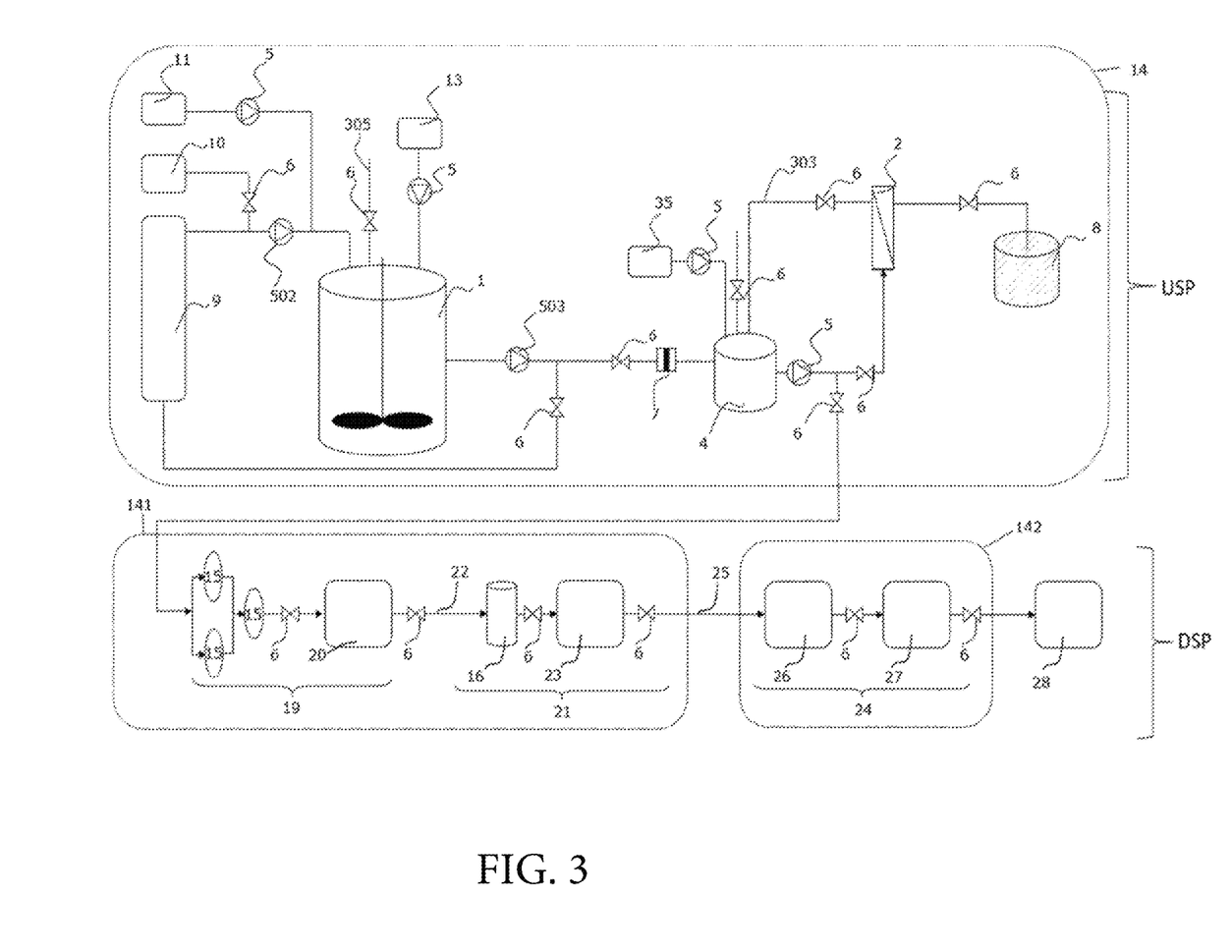
FIG. 3 shows a schematic overview of a system for producing and purifying biomolecules according to another embodiment of the disclosure.
Figure 4:
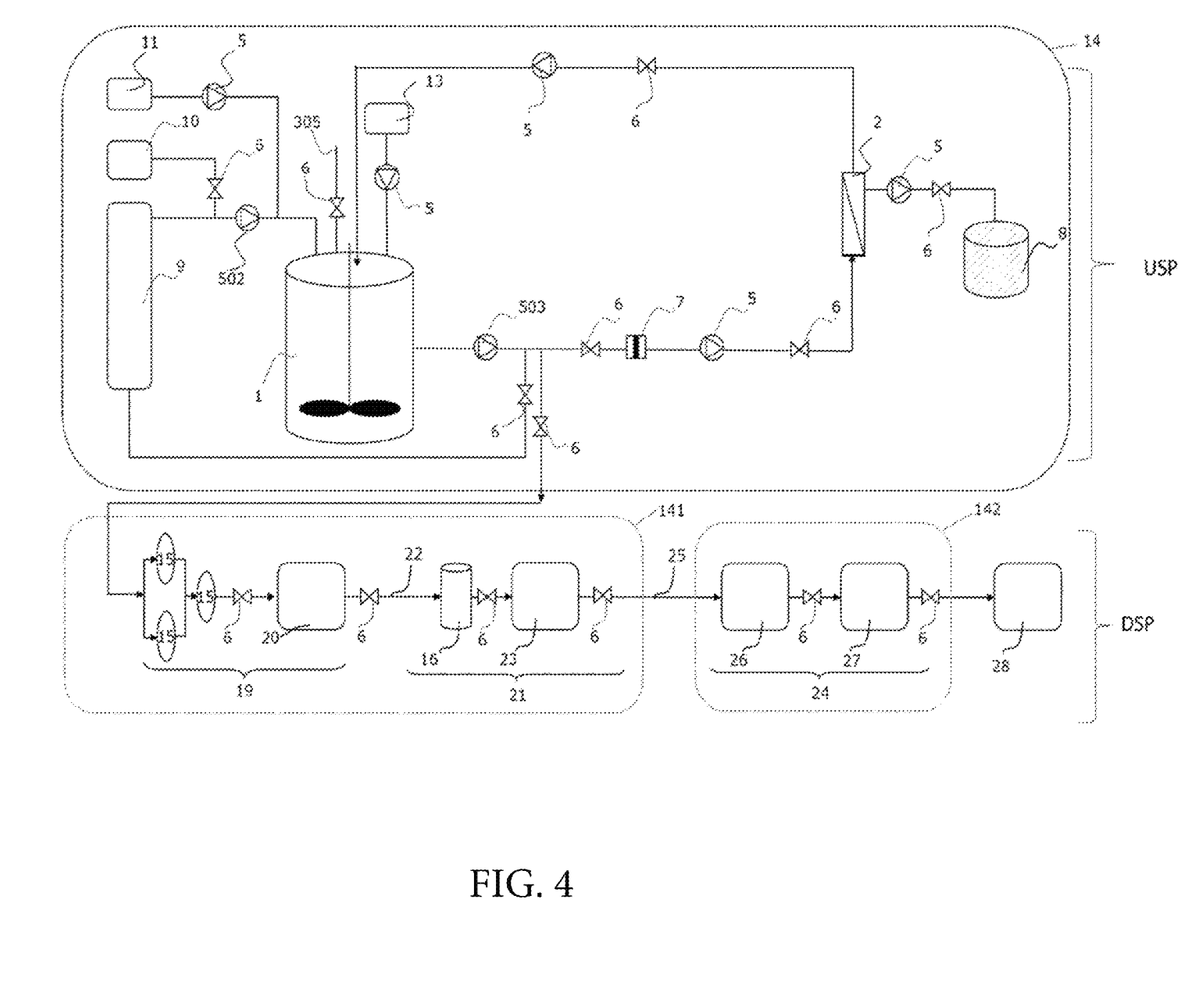
FIG. 4 shows a schematic overview of a system for producing and purifying biomolecules according to another embodiment of the disclosure.

FIGS. 3 and 4 show schematic overviews of systems for producing and purifying viruses according to embodiments of the current disclosure.

The upstream processing steps in the depicted systems include the production of virus particles in a bioreactor (1) and the concentration of a cell culture harvest using a concentrator (2). Preferably, the equipment for upstream processing steps (USP) is contained within a biosafety cabinet or isolator (14).

A pre-culture of cells suitable for the production of the desired biomolecule is obtained for inoculation in the bioreactor (1). Prior to inoculation, the bioreactor (1) is set up, provided with growth medium from a growth medium tank (9), and the medium is provided into the bioreactor (1) using at least one pump (502). By preference, the medium is pre-heated to a temperature of between 25° C. to 37° C. and mixed prior to transfer to the bioreactor. This ensures that the cells will not perceive a cold-shock when being contacted with new medium (which would negatively affect their growth) as well as ensure that all nutrients in the medium are mixed and present in the required amounts. The medium can be a liquid comprising a well-defined mixture of salts, amino acids, vitamins, carbohydrates, lipids, and one or more protein growth factors. The culture medium serves to deliver nutrients to the cell and conversely, to remove waste products and to prevent a toxic build-up of metabolic waste. The cell culture parameters are also defined prior to inoculation. In the embodiment of FIG. 3, the bioreactor (1) is further connected through conduits with the inoculum vessel (10) comprising the rinsed, detached and neutralized cell preculture in suitable growth medium, and an additives vessel (11) comprising additional additives which are known to a person skilled in the art such as for example growth factors. The bioreactor (1) can further be provided with a gas inlet (not shown) and/or outlet (305) and a base (13) inlet for regulation of the pH inside the bioreactor (1). After inoculation, the bioreactor (1) is preferably operated in batch mode for between 2 hours to 6 hours, preferably between 3 and 4 hours. In a next step, the cells are grown for a suitable time or until the desired cell density is achieved. Preferably, the bioreactor (1) is operated in perfusion mode during this cell growth period. In an embodiment, pumps (502 and 503) are provided in the system right before and after the bioreactor (1) to control flow of medium through the bioreactor (1). Prior to infection of the cells with the desired virus, the growth medium used is exchanged by dilution with growth medium suitable for viral particle production. The discarded growth medium is collected in a decontamination vessel (8). Alternatively, the growth medium is exchanged by discarding the growth medium present in the bioreactor and subsequently supplying the cells in the bioreactor with growth medium suitable for viral particle production. Infection of the cells is performed by supplying a viral seed to the bioreactor (1), the bioreactor (1) is then preferably operated in batch mode for 1-4 hours, more preferably for 2 hours.

The method for producing and purifying biomolecules according to the present disclosure makes use of pumps (5, 501, 502, 503) and valves (6), which are fitted on the conduits of the system, to induce directional flow of the liquid through the system and to allow reversible engaging and disengaging of different parts of the system.

During a next phase, viral production takes place. The bioreactor (1) is thereto operated in perfusion mode with in-line concentration. The valves and pumps between the bioreactor (1), concentrator (2) and the intermediate vessel (4), when present in the system, are thereto opened or activated. To avoid clogging of the ultrafiltration device present in the concentrator (2), the liquid is first passed through a pre-filter (7) which removes large solid particles from the liquid but is permeable to the biomolecule of interest. Preferably, the pre-filter has a pore size of approximately 125 μm and a cutoff of approximately 100 kDa. Concentration of the liquid is performed according to the presently disclosed method by passing the liquid through a concentrator (2) which is an ultrafiltration device, preferably a tangential flow filtration (TFF) device, more preferably a hollow fiber TFF. This TFF is operated in continuous mode during a limited amount of time and allows to concentrate the biomolecule of interest by discarding the permeate which contains mainly liquids and small solutes to the decontamination vessel (8), while re-circulating most of the biomolecule of interest which is present in the retentate to the intermediate vessel (4) as shown in FIG. 3 or to the bioreactor (1) as shown in FIG. 4. This allows the volume of liquid comprising the target biomolecule to be drastically reduced prior to further downstream processing.

After peaking of the viral production phase the retentate, which is recirculated between the concentrator (2) and the intermediate vessel (4) or the bioreactor (1), is harvested by collecting it in the intermediate vessel (4). The system is subsequently ran without providing new growth medium to the bioreactor (1). Once the bioreactor (1) is empty, it is in an embodiment filled again with clean medium and rinsed for a desired amount of time, after which the remaining liquid is again concentrated through the concentrator and recirculated to the intermediate vessel (4) until the desired volume reduction is achieved. Finally, the recirculated output of the concentrator (2) is harvested in said intermediate vessel (4) thereby obtaining a concentrated cell culture harvest. Alternatively, the retentate, which is recirculated between the concentrator (2) and the bioreactor (1) in the absence of an intermediate vessel (4) as shown in FIG. 4, is harvested by collecting it in the bioreactor (1). The presence of an intermediate vessel (4) as part of the system shown in FIG. 3 offers the advantage that the bioreactor (1) can be rinsed to harvest remaining liquid as described above, while the volume of this rinsing liquid can still be reduced by the concentrator prior to further downstream processing.

Optionally, the pH of the concentrated cell culture harvest is adjusted to the desired value for downstream processes using a pH adjustment solution (35) which is connected to the intermediate vessel (4) as shown in FIG. 3 or to the bioreactor (1) of FIG. 4, where the pH adjustment solution is not shown. In addition an optional endonuclease treatment can be performed on the concentrated cell culture harvest to degrade DNA and RNA present in the concentrated cell culture harvest while leaving proteins intact. An endonuclease treatment step can contribute to the prevention of aggregation in the concentrated cell culture harvest, thus providing optimal conditions for further downstream processing (DSP).

The equipment for DSP steps depicted in the systems according to FIGS. 3 and 4 include a clarification compartment (19), a chromatography compartment (21) and a viral inactivation compartment (24).

Preferably, the clarification compartment (19) and the chromatography compartment (21) are contained within a single biosafety cabinet or isolator (141). Clarification can be considered the first step of DSP and ensures removal of cell debris and other contaminants from the previously harvested retentate or cell culture harvest. The clarification compartment (19) can comprise for example a number of anion exchange depth filters (15) that remove residual solid contaminants from the product stream assuring the correct functioning of the subsequent DSP steps. The clarified cell culture harvest or clarified retentate is collected in a clarified harvest vessel (20) prior to transfer to the system's chromatography compartment (21). The chromatography compartment (21) and the clarification compartment (19) are connected by a conduit (22) facilitating liquid transport from the clarification compartment (19) to the chromatography compartment (21).

The chromatography compartment (21) provides further purification of the target biomolecule. The chromatography compartment (21) comprises a single mixed mode chromatography device (16) which offers a high binding capacity, capable of processing a large input volume in a limited number of cycles and which is suited for continuous mode operation. The chromatography compartment (21) can further comprise a chromatography harvest vessel (23). Due to the volume reduction ensured by the first part of the system, the required size of the chromatography device (16) in the chromatography compartment (21) is smaller in the disclosed system than in the systems of the prior art. Accordingly, the system allows to cut down on costs relating to expensive large chromatography equipment.

A third isolator (142) comprises a viral inactivation compartment (24), wherein the viral inactivation compartment (24) and the chromatography compartment (21) are connected by a conduit (25) facilitating liquid transport from the chromatography compartment (21) to the viral inactivation compartment (24). Viral inactivation is obtained by dilution of the purified virus that is obtained after chromatography with formaldehyde in an inactivation vessel (26). Virus inactivation can be followed by adjusting the properties of the solution comprising the inactivated virus particles in a formulation vessel (27). Adjustments may include for example adjusting salt concentration or pH of the solution.

Finally, the solution comprising high quantities of purified and inactivated viral particles can safely be collected or transferred outside the isolators in a bulk vessel (28).

Figure 5:
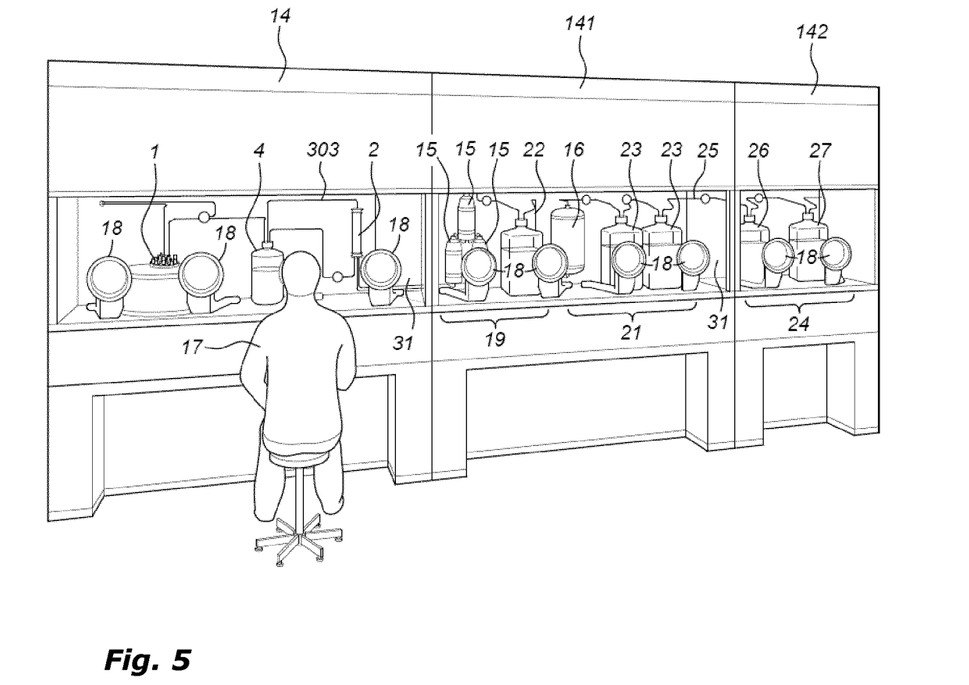
FIGS. 5 and 6 show representations of systems for producing biomolecules according to embodiments of the disclosure.
Figure 6:
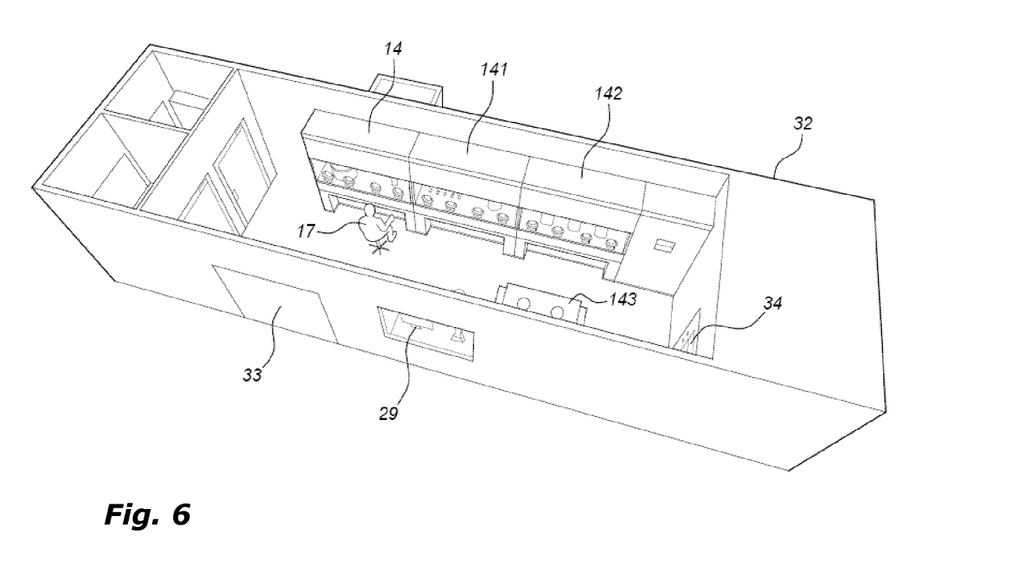

FIGS. 5 and 6 show representations of a system for producing a biomolecule such as for instance an antibody or a viral particle for formulation of a vaccine according to an embodiment of the disclosure.

FIG. 5 shows a representation of an integrated system for producing and purifying inactivated polio virus according to an embodiment of the disclosure. The system comprises several compartments which are located in three different biosafety cabinets or isolators (14, 141 and 142) within a containment enclosure (shown on FIG. 6).

The first isolator (14) comprises an upstream production and purification compartment comprising a bioreactor (1) including a chamber suitable for receiving a liquid comprising cells and viral particles, and a concentrator (2), wherein said concentrator (2) is equipped with a retentate line output (303) which collects the concentrator (2) output and which allows re-circulating of the output (retentate) to an input of an intermediate vessel (4) positioned between said concentrator (2) and said bioreactor (1).

A second isolator (141) comprises both a clarification (19) and chromatography compartment (20). The upstream production and purification compartment and the clarification compartment (19) are connected by a conduit facilitating liquid transport from the upstream production and purification compartment to the clarification compartment (19). Clarification can be considered the first step of downstream processing and ensures removal of cell debris and other contaminants from the previously harvested retentate. The clarification compartment (19) comprises a number of anion exchange depth filters (15) that remove residual solid contaminants from the product stream assuring the correct functioning of the subsequent downstream processes. The clarified cell culture harvest or clarified retentate is collected in a clarified harvest vessel (20) prior to transfer to the system's chromatography compartment (21). The implementation of a clarification compartment (19) in the system allows compact compartment operation and reduces the processing time, thus benefiting the overall economics of the biomolecule production and purification process.

The chromatography compartment (21) allows further purification of the target biomolecule. The chromatography compartment (21) and the clarification compartment (19) are connected by a conduit (22) facilitating liquid transport from the clarification compartment (19) to the chromatography compartment (21). The chromatography compartment (21) comprises a single mixed mode chromatography device (16) which offers a high binding capacity, capable of processing a large input volume in a limited number of cycles and which is suited for continuous mode operation. The chromatography compartment (21) can further comprise one or more chromatography harvest vessels (23). Due to the volume reduction ensured by the first part of the system, the required size of the chromatography device (16) in the chromatography compartment (21) is smaller than in the systems of the prior art. A 100-fold reduction of the chromatography column, for example, can be obtained in the disclosed system. Accordingly, the system allows to cut down on costs relating to expensive large chromatography equipment. Additionally, in contrast to biomolecule production and purification systems of the prior art, which usually require the presence of two consecutive chromatography devices, the current system assures equivalent biomolecule purity and yield by implementing a single-step chromatography device (16) in the chromatography compartment (21). This results in a remarkable reduction in biomolecule production footprint, production costs and production time thus enhancing the productivity, while a low process volume can be maintained throughout the system.

A third isolator (142) comprises a viral inactivation compartment (24), wherein the viral inactivation compartment (24) and the chromatography compartment (21) are connected by a conduit (25) facilitating liquid transport from the chromatography compartment (21) to the viral inactivation compartment (24). Viral inactivation is obtained by dilution of the purified virus that is obtained after chromatography with formaldehyde in an inactivation vessel (26). Virus inactivation can be followed by adjusting the properties of the solution comprising the inactivated virus particles in a formulation vessel (27).

The different isolators or safety cabinets (14,141,142) can be connected to or separated from one another by partitions (31) present between these isolators and which can be brought in an open or closed configuration. The partitions (31) shown in FIG. 5 can be made of a transparent material. Opening and closing of said partitions may also be automatically controlled by the process control device (not shown in FIG. 5) upon input signals generated by the process, such as the termination of a certain task (e.g. virus inactivation), in order to further assure the safe use of the system. Said partitions are provided with openings for allowing passage of conduits.

Due to the optimization of each compartment in the system, the compact structure of each compartment allows all compartments belonging to the system to be incorporated in a single containment enclosure (32) containing several isolators (14, 141, 142, 143) as shown in FIG. 6. The containment enclosure (32) according to the embodiment shown in FIG. 6 further comprises a number of decontamination vessels (not shown) comprising at least one waste tank where undesired material that is produced in the system or by-products of the process can be temporarily stored, a decontamination compartment, an autoclave (34) and an isolator or biosafety cabinet (143) for sample aliquoting. The optimization of each compartment in the system not only contributes to reduction of space required but also to the enhanced safety when using this system. In addition, the connections between the compartments allow the production and purification steps to be performed without having the product exit from the isolators (14, 141, 142) thus ensuring minimal safety risks.

The system includes a process control device or controller which controls and operates bioreactor parameters as well as process flow parameters. The controller further monitors and records data from one or more sensors present throughout the system and which measure for example: pH, temperature and/or DO. In addition, the process control device or controller controls opening and closing of the containment enclosure (32) entrance and/or exit (33) as well as the locking or unlocking of resealable separations or partitions (31) between the different compartments or isolators (14, 141, 142). In this embodiment, compartments are reversibly separated by resealable glass doors (31). The controller is provided with a screen (29) that allows the user to follow the process flow and measured parameters as well as to manually operate the system, e.g. by starting or stopping certain sub-processes.

An operator (17) that enters the containment enclosure (32) of the system remains outside the isolated compartments (14, 141, 142, 143). In order to allow sample taking for quality control procedures, the isolated compartments are provided with flexible sleeves (18) through which the operator (17) is allowed limited indirect access to the compartments, which content remains isolated from the operator (17). Integration of isolators (14, 141, 142, 143) and containment enclosures (32) as part of the system, renders compliance with biological safety rules simpler and less costly, reducing the risks of contamination for the environment and for the operators.

This system is suitable for use in the automated and monitored large-scale GMP production of biomolecules such as purified inactivated virus.

The invention claimed is:

1. A system for producing concentrated target biomolecules, the system comprising:
    a fixed bed bioreactor including a chamber for receiving a liquid, the bioreactor adapted for producing target biomolecules;
    a growth medium tank adapted to provide a growth medium to the bioreactor;
    an intermediate vessel;
    a concentrator adapted to separate the target biomolecule for concentration in the intermediate vessel for harvest;
    a waste container; and
    a plurality of conduits comprising
        at least one first conduit for transferring the liquid and target biomolecules between the chamber of the bioreactor and the intermediate vessel,
        at least one second conduit for transferring the liquid and target biomolecules between the intermediate vessel and the concentrator,
        at least one third conduit adapted for recycling liquid exiting the bioreactor back to the growth medium tank for redelivery into the bioreactor,
        at least one retentate conduit for collecting a retentate from said concentrator and facilitating recirculation of the retentate to an input of said intermediate vessel positioned between said concentrator and said bioreactor for collecting a concentrated target biomolecule in the intermediate vessel; and
        at least one outlet conduit from the concentrator to the waste container to discard a permeate from the concentrator.

2. The system according to claim 1, wherein said bioreactor is a perfusion bioreactor for allowing growth of cells and promoting fluid distribution and turbulence or a batch bioreactor.

3. The system according to claim 1, wherein said concentrator is an ultra- or microfiltration device.

4. The system according to claim 1, wherein a filter is positioned between said bioreactor and said intermediate vessel.

5. The system according to claim 1, wherein the system further comprises a decontamination vessel.

6. The system according to claim 1, wherein the system further comprises a clarification compartment, a chromatography compartment and/or a viral inactivation compartment.

7. The system according to claim 6, wherein said system and said one or more compartments are housed in a containment enclosure, isolator or cabinet.

8. The system of claim 1, further including a harvest conduit adapted to harvest the concentrated target biomolecule from the intermediate vessel.

9. A system for purifying target biomolecules, the system comprising: an upstream process compartment comprising a fixed-bed perfusion bioreactor including a chamber for receiving a liquid and producing target biomolecules and provided with a spiral structure for allowing growth of cells and promoting fluid distribution and turbulence; a growth medium tank adapted to provide a growth medium to the bioreactor; an intermediate vessel; a concentrator adapted to separate the target biomolecule for concentration in the intermediate vessel for harvest; a waste container; and a plurality of conduits comprising a first conduit for transferring the liquid and the target biomolecules between the chamber of the bioreactor and the intermediate vessel, a second conduit for transferring the liquid and the target biomolecules between the intermediate vessel and the concentrator, a third conduit adapted for recycling liquid exiting the bioreactor back to the growth medium tank for redelivery into the bioreactor, a retentate conduit for collecting a liquid output from said concentrator and recirculating said liquid output to an input of said intermediate vessel positioned between said concentrator and said bioreactor, an outlet conduit from the concentrator to the waste container for discarding a permeate from the concentrator, and a harvest conduit adapted to harvest concentrated target biomolecules from the intermediate vessel; a clarification compartment adapted to receive the concentrated target biomolecules; a chromatography compartment; and a viral inactivation compartment; wherein said compartments are located in one or more cabinets, isolators, or containment enclosures.

10. A system for purifying target biomolecules, the system comprising: an upstream process compartment comprising a fixed-bed perfusion bioreactor including a chamber for receiving a liquid and producing target biomolecules and provided with a spiral structure for allowing growth of cells and promoting fluid distribution and turbulence; a growth medium tank adapted to provide a growth medium to the bioreactor; an intermediate vessel; a concentrator adapted to separate the target biomolecule for concentration in the intermediate vessel for harvest; and a plurality of conduits comprising a first conduit for transferring the liquid and the target biomolecules between the chamber of the bioreactor and the intermediate vessel, a second conduit for transferring the liquid and the target biomolecules between the intermediate vessel and the concentrator, a third conduit adapted for recycling liquid exiting the bioreactor back to the growth medium tank for redelivery into the bioreactor, a retentate conduit for collecting a liquid output from said concentrator and recirculating said liquid output to an input of said intermediate vessel positioned between said concentrator and said bioreactor, an outlet conduit from the concentrator to the waste container for discarding a permeate from the concentrator, and a harvest conduit adapted to harvest concentrated target biomolecules from the intermediate vessel; and a clarification compartment adapted to receive the concentrated target biomolecules; wherein said compartments are located in one or more cabinets, isolators, or containment enclosures.

11. A system for producing concentrated target biomolecules, the system comprising:

a fixed bed bioreactor including a chamber for receiving a liquid, the bioreactor adapted for producing target biomolecules;

an intermediate vessel;

a concentrator adapted to separate the target biomolecule for concentration in the intermediate vessel for harvest;

a waste container; and a plurality of conduits comprising
- at least one first conduit for transferring the liquid and target biomolecules between the chamber of the bioreactor and the intermediate vessel,
- at least one second conduit for transferring the liquid and target biomolecules between the intermediate vessel and the concentrator,
- at least one third conduit adapted for recycling liquid exiting the bioreactor to a growth medium tank for redelivery into the bioreactor,
- at least one retentate conduit for collecting a retentate from said concentrator and facilitating recirculation of the retentate to an input of said intermediate vessel positioned between said concentrator and said bioreactor for collecting a concentrated target biomolecule in the intermediate vessel; and
- at least one outlet conduit from the concentrator to the waste container to discard a permeate from the concentrator.

\* \* \* \* \*